(12) United States Patent
Hallen et al.

(10) Patent No.: US 10,376,414 B2
(45) Date of Patent: Aug. 13, 2019

(54) UNI-PORT HYBRID GAUGE SURGICAL APPARATUSES AND METHODS

(71) Applicant: Novartis AG, Basel (CH)

(72) Inventors: Paul R. Hallen, Collyeville, TX (US); Walter J. Stark, III, Fort Worth, TX (US)

(73) Assignee: Novartis AG, Basel (CH)

( * ) Notice: Subject to any disclaimer, the term of this patent is extended or adjusted under 35 U.S.C. 154(b) by 225 days.

(21) Appl. No.: 15/376,857

(22) Filed: Dec. 13, 2016

(65) Prior Publication Data
US 2017/0165114 A1 Jun. 15, 2017

Related U.S. Application Data

(60) Provisional application No. 62/266,903, filed on Dec. 14, 2015.

(51) Int. Cl.
*A61F 9/007* (2006.01)
*A61B 1/313* (2006.01)
*A61B 3/00* (2006.01)

(52) U.S. Cl.
CPC .......... *A61F 9/00754* (2013.01); *A61B 1/313* (2013.01); *A61B 3/0008* (2013.01); *A61F 9/00736* (2013.01); *A61F 9/00781* (2013.01)

(58) Field of Classification Search
CPC ....... A61B 1/313; A61B 3/0008; A61B 90/30; A61F 9/00736; A61F 9/00754
See application file for complete search history.

(56) References Cited

U.S. PATENT DOCUMENTS

| | | |
|---|---|---|
| 3,990,453 A | 11/1976 | Douvas et al. |
| 4,011,869 A | 3/1977 | Seiler, Jr. |
| 4,168,707 A | 9/1979 | Douvas et al. |
| 4,200,106 A | 4/1980 | Douvas et al. |
| 5,201,730 A | 4/1993 | Easley et al. |
| 5,275,593 A | 1/1994 | Easley et al. |
| 5,425,730 A | 6/1995 | Luloh |
| 5,591,160 A | 1/1997 | Reynard |
| 5,651,783 A | 7/1997 | Reynard |
| 5,716,363 A | 2/1998 | Josephberg |
| 6,887,221 B1 | 5/2005 | Baillargeon et al. |
| 6,939,341 B2 | 9/2005 | Vijfvinkel |
| 7,285,107 B1 | 10/2007 | Charles |
| 7,783,346 B2 | 8/2010 | Smith et al. |
| 8,277,418 B2 | 10/2012 | Lopez et al. |
| 8,679,064 B2 | 3/2014 | Lopez et al. |

(Continued)

FOREIGN PATENT DOCUMENTS

GB 1349881 A 4/1974

OTHER PUBLICATIONS

Calhoun, et al., The Roto-Extractor in Pediatric Ophthalmology, Tr. Am. Ophth. Soc., vol. LXXIII, 1975, (14 pages).

(Continued)

*Primary Examiner* — Laura A Bouchelle (57) ABSTRACT

Systems, apparatuses, and methods include a surgical apparatus with a handle for grasping by a user and a multi-function surgical portion extending therefrom. The multi-function surgical portion may include an illuminator portion arranged to provide illumination to a surgical region of a patient during a surgical procedure, and tissue-treating portion coaxially aligned with the illuminator portion.

17 Claims, 6 Drawing Sheets

(56) References Cited

U.S. PATENT DOCUMENTS

| | | | |
|---|---|---|---|
| 8,968,347 B2 | 3/2015 | McCollam | |
| 8,979,867 B2 | 3/2015 | Peyman | |
| 9,055,885 B2 | 6/2015 | Horvath et al. | |
| 9,089,364 B2 | 7/2015 | Bhadri et al. | |
| 9,364,982 B2 | 6/2016 | Schaller | |
| 9,402,643 B2 | 8/2016 | Auld et al. | |
| 9,561,085 B2 | 2/2017 | Yadlowsky et al. | |
| 9,693,898 B2 | 7/2017 | Farley et al. | |
| 9,839,749 B2 | 12/2017 | Johnson et al. | |
| 9,956,053 B2 | 5/2018 | Diao et al. | |
| 10,010,447 B2 | 7/2018 | Kashani et al. | |
| 10,016,248 B2 | 7/2018 | Mirsepassi et al. | |
| 10,039,669 B2 | 8/2018 | Heeren | |
| 2008/0172078 A1* | 7/2008 | Svetic | A61B 17/320783 606/171 |
| 2008/0319451 A1* | 12/2008 | Zacharias | A61F 9/00736 606/107 |
| 2009/0161384 A1 | 6/2009 | Smith | |
| 2009/0163897 A1 | 6/2009 | Skinner | |
| 2012/0041461 A1* | 2/2012 | McCollam | A61F 9/00736 606/170 |
| 2012/0283523 A1* | 11/2012 | Yadlowsky | A61F 9/00763 600/249 |
| 2014/0121469 A1 | 5/2014 | Meckel et al. | |
| 2016/0074211 A1* | 3/2016 | Ko | A61B 17/3421 604/513 |
| 2017/0014023 A1 | 1/2017 | Kern | |
| 2017/0014267 A1 | 1/2017 | Kern et al. | |
| 2017/0119491 A1 | 5/2017 | Mirsepassi et al. | |
| 2017/0165114 A1 | 6/2017 | Hallen et al. | |
| 2018/0055596 A1 | 3/2018 | Johnson | |
| 2018/0132963 A1 | 5/2018 | Diao et al. | |
| 2018/0133057 A1 | 5/2018 | Diao et al. | |
| 2018/0168768 A1 | 6/2018 | Mirsepassi et al. | |
| 2018/0168861 A1 | 6/2018 | Mirsepassi et al. | |
| 2018/0338776 A1 | 11/2018 | Farley et al. | |
| 2018/0338859 A1 | 11/2018 | Mirsepassi et al. | |

OTHER PUBLICATIONS

Douvas, Microsurgical Roto-Extractor Instrument for Vitrectomy, New Research on the Aetiology and Surgery of Retinal Detachment Mod. Probl. Ophthyal., vol. 15, pp. 253-260 (Karger, Basel 1975), Port Huron, Michigan, USA (8 pages).

Museum of Vision: Collection Objects; The Foundation of the American Academy of Ophthalmology; http://www.museumofvision.org/collection/artifacts?accession=2004.004.00001; Technology dated 1970 (4 pages).

Meadow, MD, FACS; Norman B.; Vitreous history in the making; Ophthalmology Times, Jul. 15, 2013 (3 pages).

Chalam, et al., Illuminated Curved Vitrectomy Probe for Vitreoretinal Surgery, Ophthalmic Surgery, Lasers and Imaging, Nov./Dec. 2007—vol. 38 Å—Issue 6: 525-526.

Fisher et al., Inexpensive Illuminated Vitrectomy Cutter, The Journal of Retinal and Vitreous Diseases, Dec. 2003, vol. 23, Issue 6, p. 891.

"Alcon Global Vitreoretinal Product Catalog", pp. 25-40, 2014.

* cited by examiner

UNI-PORT HYBRID GAUGE SURGICAL APPARATUSES AND METHODS

TECHNICAL FIELD

The present disclosure is directed to surgical instruments, systems, and methods. More particularly, but not by way of limitation, the present disclosure is directed to surgical instruments, systems, and methods having a hybrid gauge body with functionality spaced along the instrument.

BACKGROUND

Microsurgical procedures frequently require precision cutting and/or removing of various body tissues. For example, certain ophthalmic surgical procedures, such as vitrectomy procedures, require cutting and removing portions of the vitreous humor, a transparent jelly-like material that fills the posterior segment of the eye. The vitreous humor, or vitreous, is composed of numerous microscopic fibrils that are often attached to the retina. Therefore, cutting and removing the vitreous must be done with great care to avoid traction on the retina, the separation of the retina from the choroid, a retinal tear, or, in the worst case, cutting and removal of the retina itself. The cutting and removal of membranes may be particularly difficult in some delicate operations, such as mobile tissue management (e.g., cutting and removal of vitreous near a detached portion of the retina or a retinal tear) and vitreous base dissection.

Microsurgical procedures, such as those in the posterior segment, typically require numerous incisions to access the interior of the eye. Each additional incision may create risk for complications during the procedure and/or recovery. Various tools are inserted through the incisions for use by a user, such as a surgeon or other medical professional, while performing the procedure. For example, a portion of an infusion line may be inserted through one of the incisions. The infusion line delivers fluid to the interior of the eye to maintain intraocular pressure, thereby preventing the eye from collapsing during the surgical procedure. An illuminator, which is a distinct tool from the infusion line, may be inserted through one of the other incisions. The illuminator, such as a hand-held fiber optic probe illuminator, lights the surgical field. A third tool, a surgical device, may be inserted through yet another of the incisions. The user uses the surgical device, such as a cutting probe (i.e. vitrectomy probe), to cut and remove tissue from the eye.

A three-incision (three-port) vitrectomy procedure has multiple limitations and shortcomings. For example, the surgeon must use two hands, with an instrument in each hand. In a typical procedure, a surgeon holds an illuminator with one hand and a vitrectomy probe with the other. In addition, because there are three or more incisions in the eye, the ocular anatomy may have high levels of tissue trauma. There may be a relatively high level of ocular inflammation, and there is a higher level of potential for post-operative serious adverse events. These serious events include conjunctive bleeding, hypotony (low eye pressure) due to fluid pressure loss through wounds, endophtaltmitis (sight threatening ocular infection), choroidal re-detachment and vision loss, proliferative vitreoreinopathy (PVR), enophthalmitis (internal infection), and choroidal or retina re-detachment, among others.

Because of these risks, a three-port ocular surgery may limit the magnitude and speed of vision restoration and preservation and may ultimately decrease the chance of a satisfactory patient outcome.

SUMMARY

In some exemplary aspects, the present disclosure is directed to a multi-function surgical apparatus that includes a handle for grasping by a user and an illuminator portion extending from the handle portion. The illuminator portion may be arranged to provide illumination to a surgical region of a patient during a surgical procedure. The surgical apparatus may also include a vitrectomy cutter portion extending from the handle portion and coaxially aligned with the illuminator portion. The vitrectomy cutter portion may include a port for aspirating vitreous humor. The illuminator portion may be disposed to illuminate the region about the port.

In some aspects, the surgical apparatus may include an infusion portion extending from the handle portion. The infusion portion may be arranged to introduce infusion fluid to the surgical region. The infusion portion may be concentrically disposed about the illuminator portion. In some aspects, the illuminator portion may include a fiber arranged to emit light onto the port for aspirating vitreous humor. In some aspects, the illuminator portion may have a cross-sectional width greater than a cross-sectional width of the vitrectomy cutter portion. In some aspects, the illuminator portion may include an optical fiber configured to emit light toward a surgical site treated by the vitrectomy cutter portion, in some aspects, the apparatus may include a shoulder between the illuminator portion and the vitrectomy cutter portion. The illuminator portion may be arranged to emit light from the shoulder. In some aspects, the apparatus may include an infusion portion extending from and supported by the handle portion. The infusion portion may be arranged to introduce infusion fluid to the surgical region through an infusion port disposed at a second shoulder between the outer surface of the infusion portion and the illuminator portion. In some aspects, the infusion port is annular. In some aspects, the illuminator portion includes an outer cylindrical surface having a flat portion formed at a distal end, the flat portion (not shown) being disposed and arranged to direct emitted light to extend in a fan-shape toward the cutter portion. As such, the flat portion may appear as flat on the circumference or may appear as an indented portion or notch into the outer surface.

In some exemplary aspects, the present disclosure is directed to a surgical apparatus including a handle portion for grasping by a user and a needle portion extending from the handle portion. The needle portion may include an infusion portion extending distally from the handle portion and may have a lumen and an infusion port arranged to introduce infusion fluid to a surgical region of a patient. The infusion portion may have a first cross-sectional width. The needle portion may also include an illuminator portion extending distally form the handle portion and arranged to provide illumination to the surgical region. The illuminator portion may have a second cross-sectional width different than the first cross-sectional width. The needle portion may also include a tissue-treatment portion extending distally beyond one of the illuminator portion and the infusion portion. The tissue treatment portion may have a third cross-sectional width different than the first and the second cross-sectional widths.

The surgical apparatus may include a first shoulder between the first cross-sectional width and the second cross-sectional width. The first shoulder may include the infusion port that introduces the infusion fluid to the surgical region. The second shoulder may be disposed between the second cross-sectional width and the third cross-sectional width, with the illumination being emitted from the second shoulder. In some aspects, the infusion portion, the illuminator portion, and the tissue-treatment portion are concentrically disposed. In some aspects, the infusion port is annularly shaped and concentrically disposed relative to the illuminator portion. The surgical apparatus may include a plurality of optical fibers carried by and radially spaced about the illuminator portion. The surgical apparatus may include a cannula including illumination features configured to illuminate a portion of the surgical region. The cannula may be sized to receive the infusion portion, the illuminator portion, and the tissue-treatment portion therethrough. In some aspects, the tissue-treatment portion is a vitrectomy cutter portion having an inner cutter and outer cutter and a tissue-receiving port in the outer cutter. In some aspects, the illuminator portion includes an outer cylindrical surface having a flat portion formed at a distal end. The flat portion may be disposed and arranged to direct emitted light to extend in a fan-shape toward the tissue-treatment portion.

In some exemplary aspects, the present disclosure is directed to a method for treating a patient with a multi-function surgical apparatus. The method may include introducing an infusion portion into a patient through a single incision. The infusion portion may be arranged to introduce infusion fluid to the surgical region, an illuminator portion arranged to provide illumination to a portion of the patient, and a tissue-treatment portion configured to engage tissue or liquid within the patient. The method also may include simultaneously introducing an infusion fluid through the infusion portion, introducing illumination with the illuminator portion, and treating the patient with the tissue treatment portion.

The method also may include introducing the infusion fluid from an infusion port in a shoulder between the infusion portion and the illuminator portion and may include introducing the illumination from a shoulder between the illuminator portion and the tissue treatment portion.

It is to be understood that both the foregoing general description and the following drawings and detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following.

BRIEF DESCRIPTION OF THE DRAWINGS

The accompanying drawings illustrate implementations of the systems, devices, and methods disclosed herein and together with the description, serve to explain the principles of the present disclosure.

These figures will be better understood by reference to the following Detailed Description.

DETAILED DESCRIPTION

For the purposes of promoting an understanding of the principles of the present disclosure, reference will now be made to the implementations illustrated in the drawings and specific language will be used to describe them. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In addition, this disclosure describes some elements or features in detail with respect to one or more implementations or Figures, when those same elements or features appear in subsequent Figures, without such a high level of detail. It is fully contemplated that the features, components, and/or steps described with respect to one or more implementations or Figures may be combined with the features, components, and/or steps described with respect to other implementations or Figures of the preset disclosure. For simplicity, in some instances the same or similar reference numbers are used throughout the drawings to refer to the same or like parts.

The present disclosure relates generally to surgical instruments, systems, and methods for performing a minimally invasive surgical procedure. In some implementations, the surgical instrument is a single-port, multi-function instrument. Single-port is intended to mean that a single instrument simultaneously performs multiple surgical functions through a single port or incision. The instrument, depending on the embodiments, may combine functions of multiple instruments in a manner that more efficiently performs a surgical process, is less invasive to the patient, and/or renders the technique easier for the surgeon. Some embodiments of the multi-function instrument combine functions of a vitrectomy probe, an illuminator, and an infusion line into a single instrument. Because these are combined into a single instrument, the surgeon can perform the vitrectomy with sufficient illumination and infusion with a single hand. The second hand is then free to perform other processes or other elements of the surgery. For example, the second hand may use a second surgical tool that would double utility (e.g., external scleral depression). Also, it would reduce the incisions from three (including separate incisions for illumination, for infusion, and for the vitrectomy probe) to one. Fewer incisions may reduce the opportunity for infection, may reduce the scar tissue, introduce less patient trauma to the tissue, and may speed patient recovery time.

In some embodiments, the multi-function instrument may be utilized with an illuminated cannula that provides additional illumination to the surgical site. A multi-function instrument may then be introduced through the cannula to the surgical treatment area in the patient.

Figure 1:
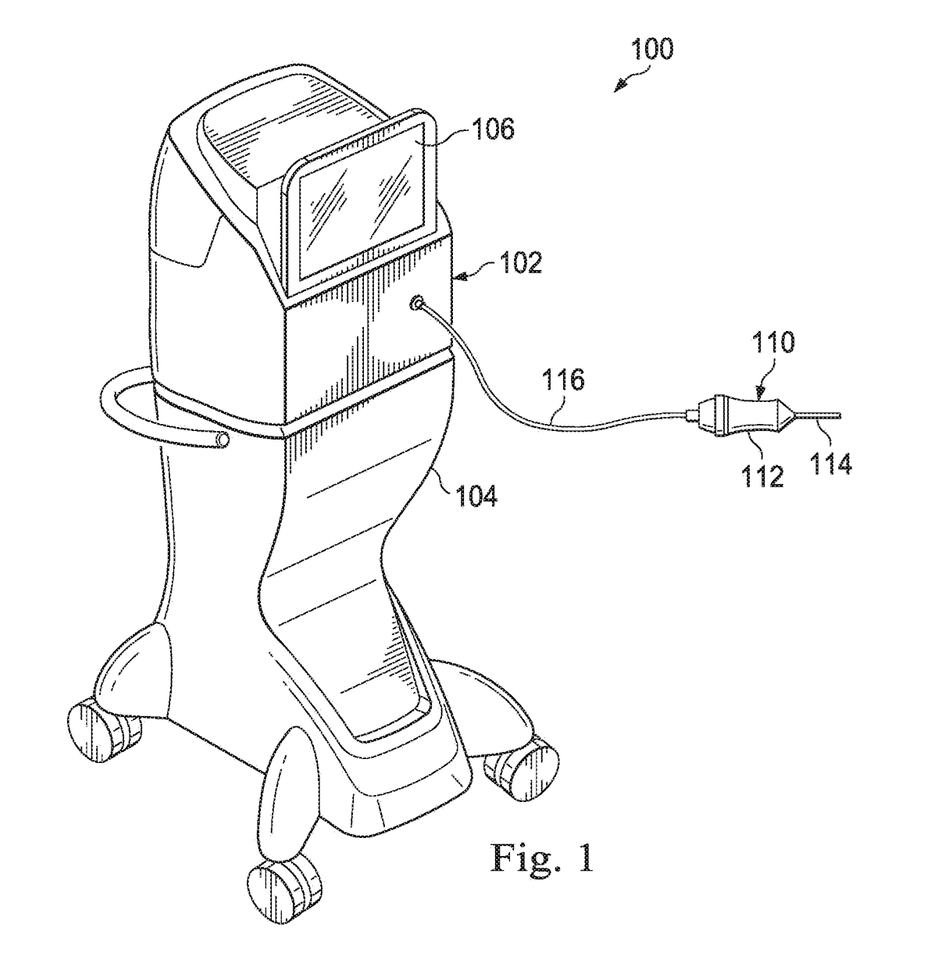
FIG. 1 is an illustration of an ophthalmic surgical apparatus according to an exemplary aspect.

FIG. 1 illustrates a multi-function vitrectomy surgical apparatus, generally designated by the reference numeral 100, according to an exemplary embodiment. The surgical apparatus 100 includes a console 102 that includes a base housing 104 and an associated display screen 106 showing data relating to system operation and performance during a vitrectomy surgical procedure. The console 102 may include multiple functions, subassemblies, equipment, and other capabilities for performing one or more surgical treatment procedures, including vitrectomy procedures.

In this embodiment, the surgical apparatus 100 includes a multi-function instrument shown as a vitrectomy probe 110 for performing vitrectomy procedures. Here, the vitrectomy probe 110 may be a uni-port hybrid gauge instrument that performs a number of functions, including illumination, infusion, and the vitrectomy treatment for the removal of tissue, such as vitreous humor or removal or irrigation of infusion fluid introduced into a chamber in a patient. The vitrectomy probe is a uni-port probe because multiple functions may be performed through a single port. The vitrectomy probe 110 includes both a handle portion 112 and a needle portion 114. The handle portion 112 attaches to the console 102 via a cable 116 that may be configured to provide irrigation capabilities, aspiration capabilities, power, or other elements or to the vitrectomy probe 110.

Figure 2:
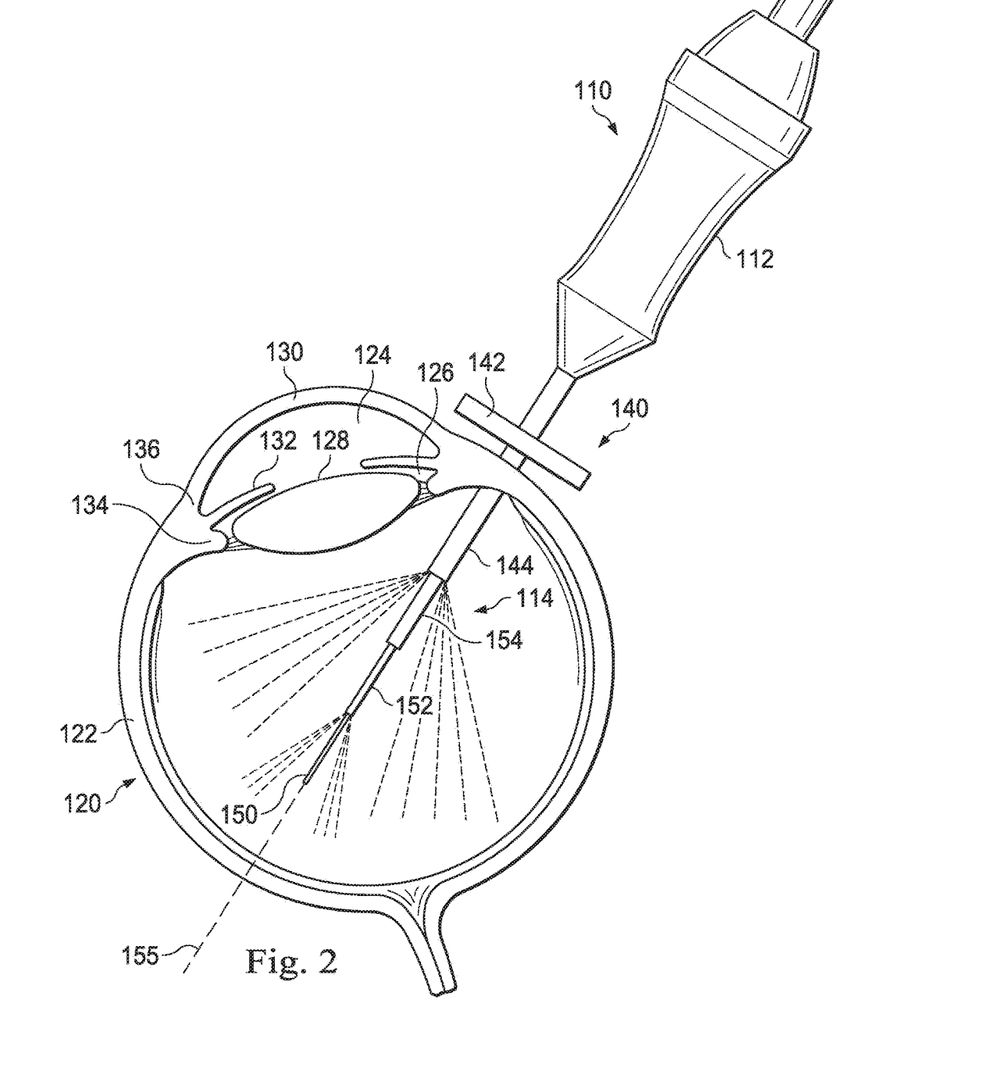
FIG. 2 shows an example hybrid gauge needle in situ in an eye.

FIG. 2 shows a portion of the needle portion 114 of the vitrectomy probe 110 in greater detail. It is shown as it may be disposed during a surgical procedure protruding into patient tissue, such as an eye 120. The eye 120 includes a globe 122 with an anterior chamber 124, a posterior segment 126 and representations of a lens 128, cornea 130, iris 132, ciliary bodies 134, and trabecular meshwork 136. The needle portion 114 of the vitrectomy probe 110 extends through surface tissue into the posterior segment 126. FIG. 2 also shows a cannula 140 that extends from the exterior of the globe 122 into the posterior segment 126.

The cannula 140 includes a hub 142 and a main body 144. In this embodiment, the cannula 140 includes a valve (not shown) disposed therein to limit the egress of fluids, including vitreous, from the posterior segment 126 through the main body 144 and the hub 142. The hub 142 is configured to rest on the tissue surface and prevent the cannula 140 from entering further into the posterior segment 126. In this embodiment, the main body 144 includes an illumination feature that also provides illumination of the surgical region, including the surgical site.

The illumination features on the cannula 140 may be formed of one or more optical fibers that carry light from a light source and emit the light in the surgical region. Some implementations include one or more optical fibers disposed along the main body of the cannula, along the exterior surface, the interior surface, or embedded within the main body in a preformed groove, passage, or other feature. The optical fibers may direct light from a light source, such as on the console 102 (FIG. 1), on the hub 142, or elsewhere disposed, and emit the light adjacent the distal end of the main body 144. This may permit the user to visualize the interior of the surgical site using a surgical microscope or other visualization system.

As can be seen, the needle portion 114 includes a tissue-treating portion, shown here as a cutter portion 150. The needle portion also includes an illuminator portion 152 and an infusion portion 154, all of which are coaxially aligned along a central axis 155. The needle portion 114 is a hybrid gauge system because it includes an exterior surface having different cross-section widths. For example, in the embodiment shown, the needle portion 114 steps progressively down in diameter or cross-section from the infusion portion 154, to the illuminator portion 152, and to the cutter portion 150.

The cutter portion 150 preforms the vitrectomy function of opening and closing a port to detach vitreous humor from the retina and to aspirate the vitreous humor from the posterior segment 126. The illuminator portion 152 is embedded with illumination elements, such as an optical fiber, and may provide additional light to the surgical site from a location close in proximity to cutting elements of the cutter portion 150. The infusion portion 154 is configured to provide infusion fluid to maintain intraocular pressure during a surgical process. Each of these is described in greater detail below.

Figure 3:
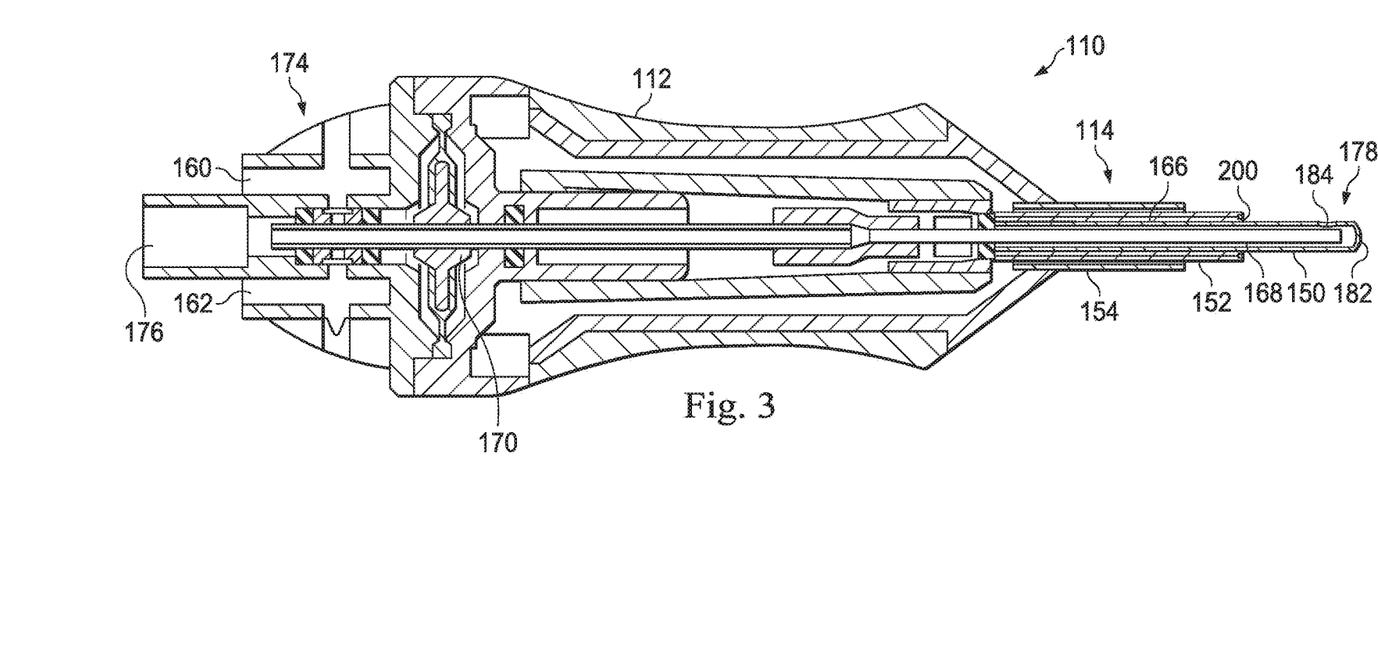
FIG. 3 shows a cross-sectional view of an example vitrectomy probe with a hybrid gauge needle.

FIG. 3 shows a cross-sectional illustration of the exemplary vitrectomy probe 110. In this example, the vitrectomy probe 110 is a pneumatically driven probe that operates by receiving pneumatic pressure alternating through first and second air supply ports 160 and 162. The needle portion 114 of the vitrectomy probe 110 includes the cutter portion 150 comprising an outer cutting tube 166, an inner cutting tube 168, and a probe actuator shown here as a reciprocating air driven diaphragm 170, all partially encased by the handle portion 112. The handle portion 112 includes an end piece 174 at the vitrectomy probe proximal end with the first and second air supply ports 160, 162 and one suction port 176.

Figure 4A:
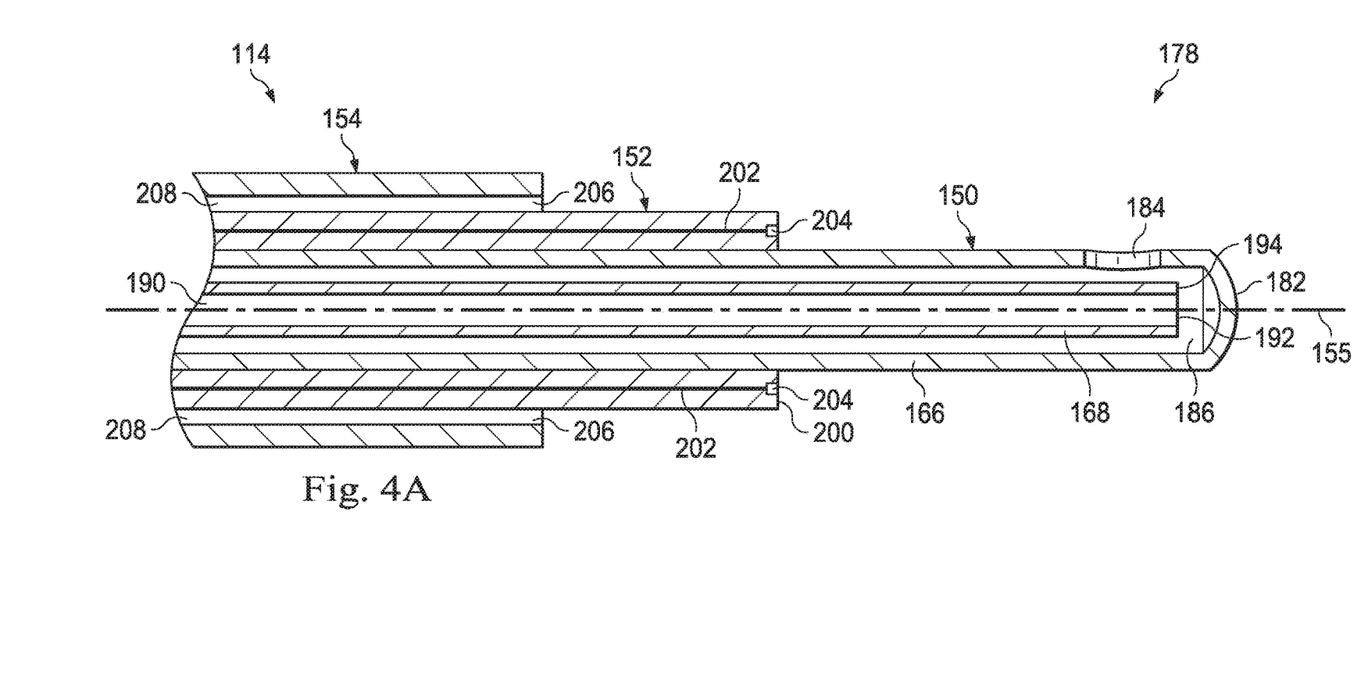
FIG. 4A shows a more detailed cross-sectional view of a needle of an example hybrid gauge needle.

As can be seen, the cutter portion 150 extends from the handle portion and includes a distal end 178. FIG. 4A shows the distal end 178 of the cutter portion 150 in greater detail. The outer cutting tube 166 has a closed end 182 and an outer port 184 that receives tissue, such as ophthalmic tissue. The outer port 184 is in fluid communication with an inner channel 186 of the outer cutting tube 166. The inner cutting tube 168 is located within the inner channel 186 of the outer cutting tube 166. The inner cutting tube 168 has an inner bore 190, an open end 192, and a cutting surface 194. The inner bore 190 is in fluid communication with an aspiration line (not shown) that connects to a vacuum pressure that pulls tissue into the outer port 184 when the inner cutting tube 168 is located away from the outer port 184. The inner cutting tube 168 moves within the inner channel 186 of the outer cutting tube 166 to cut tissue that is pulled into the outer port 184 by the aspiration system. The ophthalmic tissue received by the outer port 184 is preferably vitreous or membranes.

When used to cut tissue, the inner cutting tube 168 is initially moved away from the outer port 184 and the vacuum pressure pulls tissue into the outer port 184 and the inner channel 186. The inner cutting tube 168 then moves toward the outer port 184 and severs the tissue within the inner channel 186. The severed tissue is pulled through the inner bore 190 of the inner cutting tube 168 by the aspiration system. The inner cutting tube 168 then moves away from the outer port 184, and the cutting process is repeated. A cutting cycle includes moving the inner cutting tube 168 to open the outer port 184 and then moving the inner cutting tube 168 to close the outer port 184 to initiate the cut and return the inner cutting tube 168 to its starting position for the next cutting cycle.

With reference now to both FIGS. 3 and 4, the inner cutting tube 168 is driven by air pressure directed on opposing sides of the diaphragm 170. In one example of operation, if air pressure is increased at the first port 160, the diaphragm 170 will move distally, displacing the inner cutting tube 168 relative to the outer cutting tube 166, thereby closing the tissue-receiving outer port 184 of the outer cutting tube 166. This cuts any vitreous material which may have been aspirated into the tissue-receiving outer port 184. Venting the pressure at the first port 160 and increasing the pressure at the second air supply port 162 will move the diaphragm 170 proximally, opening the tissue-receiving outer port 184 so that it can draw in new vitreous material to be cut. It's worth noting that other embodiments include alternative probe actuators. For example, some actuator embodiments include a piston motor in place of a diaphragm. In this type of embodiment, the cutter portion 150 is arranged so that movement of the piston also moves the inner cutting tube 168 of the cutter portion 150. Yet other actuator embodiments include other types of pneumatic or electric motors that drive the inner cutting tube 168.

In the hybrid gauge needle portion 114 shown, the cutter portion 150 forms the distal end and has a smaller diameter, and therefore a smaller cross-sectional distance, than the illuminator portion 152 or the infusion portion 154. While the diameter may be any suitable size, in some embodiments, the diameter is selected to be within a range of about 20-40 gauge, and may be selected to be within a range of about 25-30 gauge. In some embodiments, the diameter of the cutter portion 150 is selected to be about 27 gauge.

Although described as a cutter portion, the tissue-treating portion may be formed of other instruments or tools configured to treat tissue during a surgical procedure. In some embodiments, the tissue treating portion is a forceps, a scraper, or other tool that may be used to perform a surgical treatment.

The illuminator portion 152 is disposed adjacent the cutter portion 150 and is arranged to provide illuminating light to the surgical site so that the user can see the surgical site. In this embodiment, the illuminator portion emits light in the direction of the cutter portion so that the region being treated by the cutter portion is illuminated.

In the exemplary embodiment shown, the illuminator portion 152 has a larger diameter, and therefore a larger cross-sectional distance, and is coaxial with the cutter portion 150. Accordingly, an illumination shoulder 200 provides a step from the cutter portion diameter to the illuminator portion diameter. The shoulder 200 may be a smooth increase, such as a tapered shoulder region, or may be a sharp step as shown in FIG. 4A, such that the shoulder surface is perpendicular to the central axis 155 of the needle portion 114. The shoulder 200 may be spaced from the surface of the cutter portion 150 so that light emitted from the shoulder 200 may illuminate along the cutter portion 150, as well as away from the cutter portion 150.

In some embodiments, the illuminator portion 152 may comprise one or more optical fibers 202 that are embedded within or disposed along the illuminator portion 152. The optical fibers 202 may extend to a light source, such as a light source on the console 102 (FIG. 1). The illuminator portion 152 may emit light from a single point or from a plurality of points about the circumference of the illuminator portion. In the embodiment shown in FIG. 4A, two optical fibers 202 are spaced apart from one another by 180 degrees about the central axis 155 of the needle portion 114. In other embodiments, the optical fibers 202 may be spaced at other angles. Some embodiments have three optical fibers disposed 120 degrees apart from one another about the circumference of the illuminator portion 152. In this embodiment, the optical fibers include an emitting end 204 that is disposed flush with or adjacent to the shoulder 200. The multi-gauge nature of the exemplary embodiment in FIG. 4A enables the emitting ends 204 of the optical fibers to be spaced apart from the surface of the cutter portion 150. In some embodiments, at least one optical fiber 202 has an emitting end that is axially aligned with the outer port 184, in the manner shown in FIG. 4A. Accordingly, light emitted from this optical fiber may enable the user to perceive the vitreous and liquid as it flows toward and into the port during a surgical procedure.

Figure 4B:
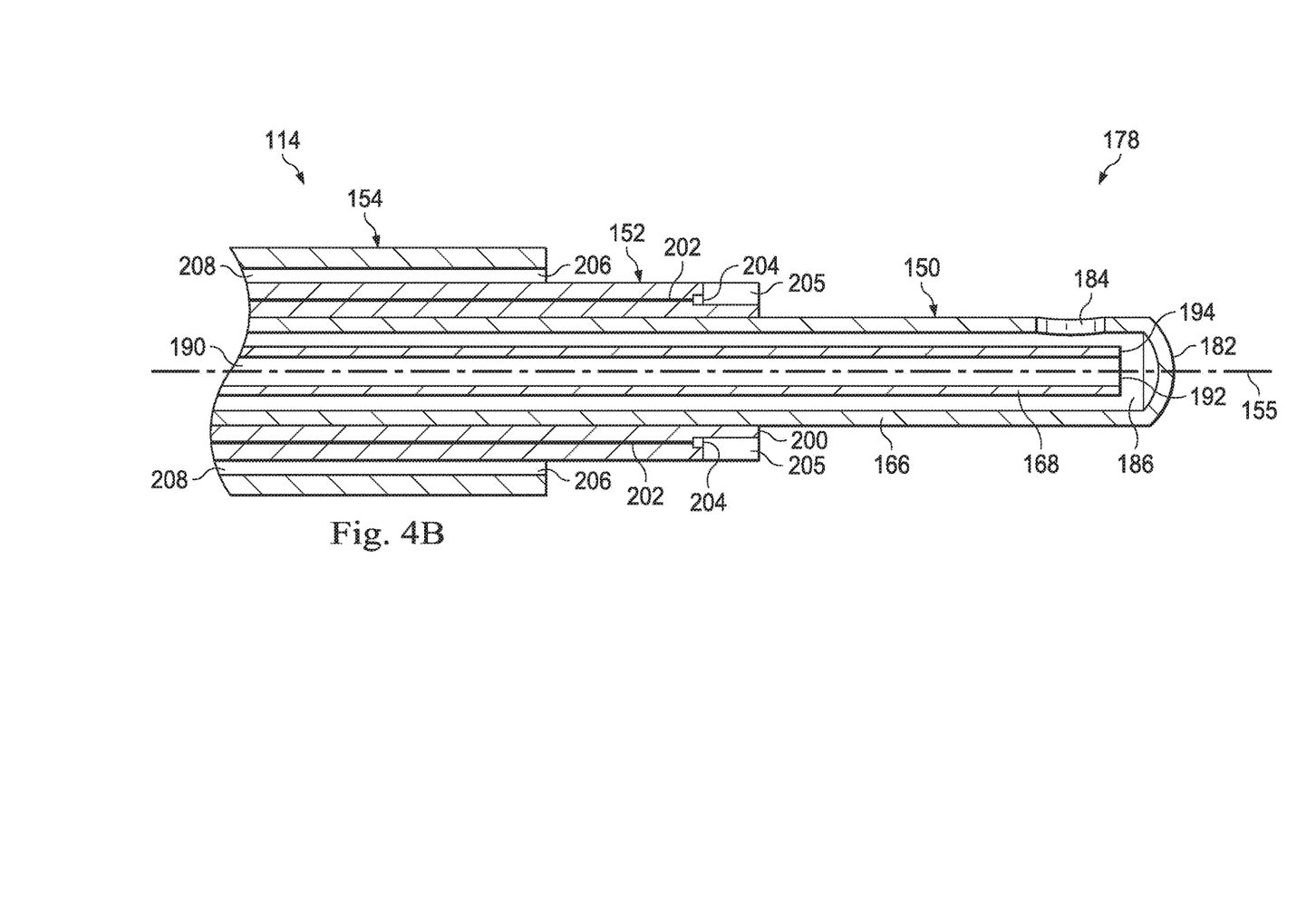
FIG. 4B shows the cross sectional view of the needle of FIG. 4A with a slot for an illumination portion.

Some needle portion embodiments include features adjacent the emitting end 204 that permit the light to be emitted at a wide angle, and in some embodiments, in a fan-shape. For example, some embodiments include the optical fiber 202 disposed so that the emitting end 204 is disposed proximal of the shoulder 200 and is therefore protected by the surrounding structure. The illuminator portion 152 may be formed to provide an illumination pathway that permits the light to illuminate the area about the surgical site. In some examples, the illuminator portion 152 comprises a V-shaped cutout in its outer surface adjacent the shoulder 200. Because of the cutout, light emitted may be permitted to shine in a fan-shape with a wide-angle even with the emitting end 204 being disposed proximal (in the direction toward the handle portion) of the shoulder 200. In other embodiments, the illuminator portion 152 includes an outer cylindrical surface having a flat portion formed at a distal end. The emitting end 204 may be disposed between the portion and the outer surface. In some embodiments, the flat portion may appear as a flat harmed on the circumference of the illuminator portion 152 or may be formed as an indented portion or notch (shown as 205 in FIG. 4B) into the outer surface. The indent or notch 205 may have a V-shape with the open end of the V facing toward the distal cutter portion to direct emitted light in a fan-shape toward the cutter portion.

In the hybrid gauge needle portion 114 shown, the illuminator portion 152 has a smaller diameter than the infusion portion 154 and has a larger diameter than the cutter portion 150. While the diameter of the illuminator portion 152 may be any suitable size, in some embodiments, the diameter is selected to be within a range of about 20-40 gauge, and may be selected to be within a range of about 20-28 gauge. In some embodiments, the diameter of the illuminator portion 152 is selected to be about 25 gauge.

The infusion portion 154 is arranged as an outer surface of the needle portion 114 and is disposed adjacent to the illuminator portion 152. The infusion portion 154 acts to direct infusion fluid into the surgical region. Depending on the embodiment, the infusion portion 154 may harm or may include one or more infusion ports 206 that direct infusion fluid into the surgical region. In some embodiments, the infusion portion 154 and the illuminator portion 152 together form one or more lumens 208 leading to the infusion ports 206. In some embodiments, the lumen is a single, annular lumen formed between the infusion portion 154 and the illuminator portion 152. In other embodiments, a plurality of lumens spaced about the illuminator portion 152 is formed into the infusion portion 154. For example, one embodiment includes two lumens spaced 180 degrees apart. Another embodiment includes three lumens spaced 120 degrees apart. In some embodiments, the lumens are formed as grooves in the inner surface of the infusion portion 154. Fluid provided from the console 102 (FIG. 1) may be fed to the vitrectomy probe 110 and then to the lumen 208 and out of the infusion port 206. For example, the console may include a fluid source such as a reservoir of fluid and a pump or other flow mechanism in fluid communication with such a reservoir.

In the hybrid gauge needle portion 114 shown, the infusion portion 154 has a larger diameter than the illuminator portion 152 and has a larger diameter than the cutter portion 150. It therefore has a larger cross-sectional distance than the illuminator portion 152. While the diameter of the infusion portion 154 may be any suitable size, in some embodiments, the diameter is selected to be within a range of about 15-30 gauge, and may be selected to be within a range of about 18-27 gauge. In some embodiments, the diameter of the infusion portion 154 is selected to be about 23 gauge. While described in terms of diameter, some embodiments have non-circular outer surfaces, and therefore the cross-sectional distance may be used in place of diameter. For example, some instruments may have an oval cross-section or other shape.

Figure 5:
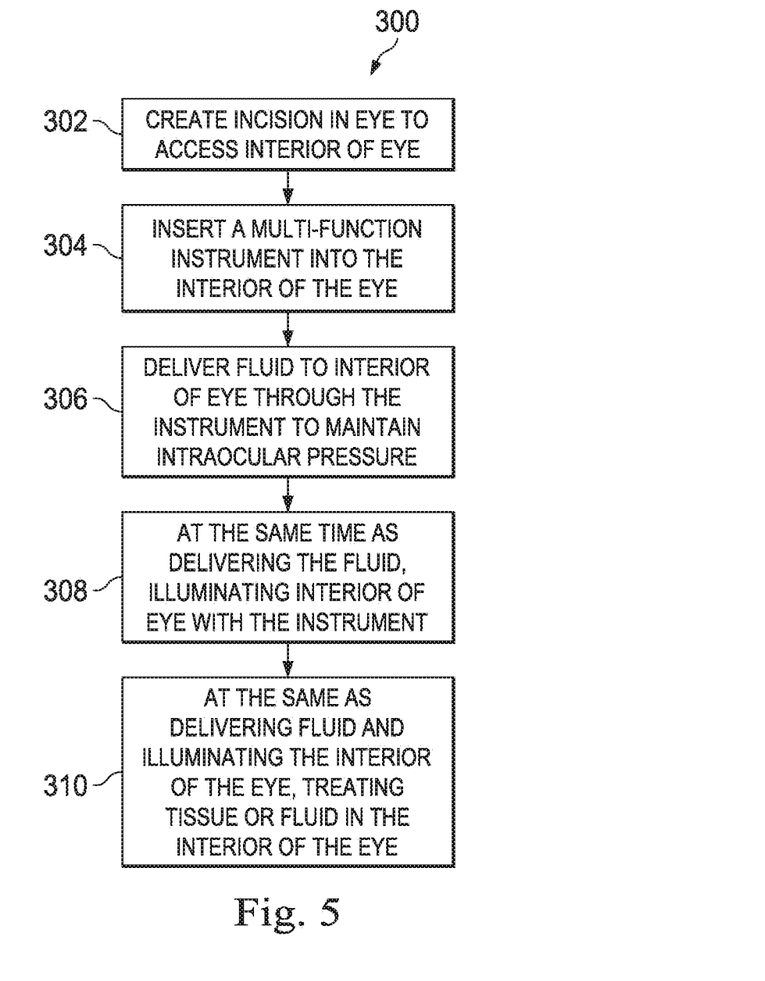
FIG. 5 shows a flow chart of an example method of performing a surgery.

FIG. 5 illustrates an exemplary method 300 of performing an ophthalmic surgical procedure. As illustrated, the method 300 includes a number of enumerated steps. Implementations of the method 300 may include additional steps before, after, and in between the enumerated steps. In some implementations, one or more of the enumerated steps may be omitted or performed in a different order.

The method may begin at 302 and includes creating an incision in the eye to access the interior, such as a posterior segment of the eye. Depending upon the technique, the user may create the incisions through the sclera in the pars plana using a trocar. The incision may be referred to as a sclerotomy. A trocar blade is then removed, with the trocar cannula remaining within the incision and defining a lumen into the posterior segment of the eye, such as the vitreous chamber. In some embodiments, the trocar cannula includes illumination features, such as one or more optical illumination fibers that carry light from a light source and emit light into the eye. As indicated above, the cannula may be a valve cannula that prevents fluids and/or tissue, such as vitreous humor, from flowing through the cannula port. This helps maintain the intraocular pressure in the eye at an acceptable level. Depending on the embodiment, the light source on the cannula may be disposed on the console (FIG. 1), on a surgical microscope, or elsewhere about the surgical room. Some embodiments include the source on the cannula itself.

At 304, the method 300 includes inserting a multi-function instrument, such as the vitrectomy probe 110, through the lumen of the cannula and into the interior of the eye. In some techniques, this includes inserting a hybrid gauge instrument that includes a tissue-treating portion (e.g., a cutter portion), an illuminator portion, and an infusion portion, with the cutter portion having a first gauge size, the illuminator portion having a second, larger gauge size, and an infusion portion having a third larger gauge size. Accordingly, through a single-port access cannula, a user can perform a vitrectomy procedure, illuminate the surgical site and/or the region to be treated, and infuse fluid to maintain the intraocular eye pressure at a desired level. This reduces the number of access incisions and the number of instruments used in the surgery and provides numerous advantages to the both the user and the patient.

At 306, with the instrument protruding into the interior of the eye, the user may deliver fluid to the interior of the eye to maintain intraocular pressure. Delivering fluid may include activating an infusion mode on the console or other infusion fluid source, and injecting fluid through the infusion portion of instrument into the interior of the eye. Injecting fluid through the infusion portion may include injecting fluid from a lumen or port in the infusion portion. Depending on the structural arrangement, the lumen or port may be formed within the infusion portion only, or alternatively, may be formed between a surface of the infusion portion and a surface of the illuminator portion. In some embodiments, the infusion port is annular shaped and coaxial with an axis of the instrument, while in other embodiments, the infusion portion includes one port or a plurality of ports spaced about the axis of the instrument. The infusion fluid may be any fluid described herein or that is otherwise suitable for flushing, treating, or maintaining pressure within the eye.

At 308, at the same time as delivering infusion fluid to the eye, the instrument may illuminate the interior of the eye with the illuminator portion. The illuminator portion may illuminate the surgical site and in some embodiments, may illuminate the tissue-treating portion, such as the cutter portion, of the instrument. In embodiments where the surgical treatment end of the instrument is a cutter portion, this technique may include illuminating a port of the cutter portion so that tissue and fluid being aspirated into the port can be visually perceived by the user. As described herein, the illuminator portion may include powering a light source at the console, or may include a light source elsewhere disposed about the surgical room. In some embodiments, the light source is disposed on the instrument itself. Illuminating the interior of the eye with the light source may include illumination optical fiber tips disposed at or adjacent a shoulder separating a cutter portion from an illuminator portion. The steps 306 and 308 may be performed simultaneously.

At step 310, and at the same time as delivering fluid and illuminating the interior of the eye, the method may include treating tissue or fluid on the interior of the eye. Treating the tissue may be done in a variety of ways using the instrument. When the tissue-treating portion of the multi-function instrument is a cutter portion, this may include performing a vitrectomy procedure on the eye. It may also include performing other treatments on the eye when the tissue-treating portion of the cutter portion is an alternative tissue or treatment implement.

Upon conclusion of the surgical procedure, the multi-function instrument may be withdrawn. Because the multi-function instrument combines multiple functionality into a single instrument, the instrument may be invasive and multiple functions may be accomplished through only a single incision. This may streamline the surgery, provide for easier instrument handling by the user, and may provide better patient outcome.

While the systems and methods herein refer to a vitrectomy probe, it should be understood that the multi-function instrument may include illumination, infusion, and alternative tool portions for treating tissue. For example, some embodiments include forceps as tissue-treatment portions, with hybrid gauge integrated infusion and illumination as described herein. Other tissue-treatment portions include scissors, laser probes, aspiration probes, diathermy probes, flex loop probes, fluid injection devices, human lens fragmentation probes, endoscopes, among others. All of these may be used with hybrid gauge integrated infusion and/or illumination as described herein. Hand-held fiberoptics may also include hybrid gauge integrated infusion and/or illumination as described herein.

Persons of ordinary skill in the art will appreciate that the implementations encompassed by the present disclosure are not limited to the particular exemplary implementations described above. In that regard, although illustrative implementations have been shown and described, a wide range of modification, change, combination, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:
1. A multi-function surgical apparatus, comprising:
a handle for grasping by a user;
an illuminator portion extending from a portion of the handle and arranged to provide illumination to a surgical region of a patient during a surgical procedure; and a vitrectomy cutter portion extending from the handle portion and coaxially aligned with the illuminator portion, the vitrectomy cutter portion including a port for aspirating vitreous humor, the illuminator portion being disposed to illuminate the surgical region about the port;

a cannula including illumination features configured to illuminate a portion of the surgical region, the cannula being sized to receive the illuminator portion and the vitrectomy cutter portion therethrough.

2. The surgical apparatus of claim 1, comprising an infusion portion extending from the handle portion, the infusion portion being arranged to introduce infusion fluid to the surgical region.

3. The surgical apparatus of claim 1, wherein the illuminator portion comprises a fiber arranged to emit light onto the port for aspirating the vitreous humor.

4. The surgical apparatus of claim 3, wherein the illuminator portion is concentrically disposed about the vitrectomy cutter portion.

5. The surgical apparatus of claim 1, wherein the illuminator portion has a cross-sectional width greater than a cross-sectional width of the vitrectomy cutter portion.

6. The surgical apparatus of claim 1, wherein the illuminator portion comprises an optical fiber configured to emit light toward a surgical site treated by the vitrectomy cutter portion.

7. The surgical apparatus of claim 1, further comprising a shoulder between the illuminator portion and the vitrectomy cutter portion, the illuminator portion being arranged to emit light from the shoulder.

8. The surgical apparatus of claim 1, further comprising an infusion portion extending from and supported by the handle portion, the infusion portion being arranged to introduce infusion fluid to the surgical region through an infusion port disposed at a second shoulder between an outer surface of the infusion portion and the illuminator portion.

9. The surgical apparatus of claim 8, wherein the infusion port is annular.

10. A surgical apparatus, comprising:
a handle portion for grasping by a user; and
a needle portion extending from the handle portion, comprising:
an infusion portion extending distally from the handle portion and having a lumen and an infusion port arranged to introduce infusion fluid to a surgical region of a patient, the infusion portion having a first cross-sectional width;
an illuminator portion extending distally from the handle portion and arranged to provide illumination to the surgical region, the illuminator portion having a second cross-sectional width different than the first cross-sectional width; and
a tissue-treatment portion extending distally beyond one of the illuminator portion and the infusion portion, the tissue-treatment portion having a third cross-sectional width different than the first and the second cross-sectional widths; and
a cannula including illumination features configured to illuminate a portion of the surgical region, the cannula being sized to receive the infusion portion, the illuminator portion, and the tissue-treatment portion therethrough.

11. A surgical apparatus of claim 10, comprising:
a first shoulder between the first cross-sectional width and the second cross-sectional width, the first shoulder including the infusion port that introduces the infusion fluid to the surgical region; and
a second shoulder between the second cross-sectional width and the third cross-sectional width, the illumination being emitted from the second shoulder.

12. The surgical apparatus of claim 10, wherein the infusion portion, the illuminator portion, and the tissue-treatment portion are concentrically disposed.

13. The surgical apparatus of claim 10, wherein the infusion port is annularly shaped and concentrically disposed relative to the illuminator portion.

14. The surgical apparatus of claim 13, comprising a plurality of optical fibers carried by and radially spaced about the illuminator portion.

15. The surgical apparatus of claim 10, wherein the tissue-treatment portion is a vitrectomy cutter portion having an inner cutter and outer cutter and a tissue-receiving port in the outer cutter.

16. A method for treating a patient with a multi-function surgical apparatus, comprising:
introducing into a patient through a single incision, an infusion portion arranged to introduce infusion fluid to a surgical region, an illuminator portion arranged to provide illumination to a portion of the patient, a tissue-treatment portion configured to engage tissue or liquid within the patient, and a cannula including illumination features configured to illuminate a portion of the surgical region, the cannula being sized to receive the infusion portion, the illuminator portion, and the tissue-treatment portion therethrough; and
simultaneously performing the following:
introducing an infusion fluid through the infusion portion;
introducing illumination with the illuminator portion; and
treating the patient with the tissue-treatment portion.

17. The method of claim 16, wherein
introducing the infusion fluid through the infusion portion comprises introducing the infusion fluid from an infusion port in a shoulder between the infusion portion and the illuminator portion; and
introducing the illumination comprises introducing the illumination from a shoulder between the illuminator portion and the tissue-treatment portion.

* * * * *